(12) United States Patent
Lorch

(10) Patent No.: US 8,381,742 B2
(45) Date of Patent: Feb. 26, 2013

(54) DENTAL FLOSS

(76) Inventor: Leonard G. Lorch, Mill Valley, CA (US)

( * ) Notice: Subject to any disclaimer, the term of this patent is extended or adjusted under 35 U.S.C. 154(b) by 4 days.

(21) Appl. No.: 13/012,105

(22) Filed: Jan. 24, 2011

(65) Prior Publication Data

US 2011/0240057 A1 Oct. 6, 2011

(51) Int. Cl.
*A61C 15/00* (2006.01)
(52) U.S. Cl. ........................................... 132/323
(58) Field of Classification Search ........... 132/321–329
See application file for complete search history.

(56) References Cited

U.S. PATENT DOCUMENTS

| | | |
|---|---|---|
| 1,929,906 A | 10/1933 | Skokowski |
| 2,029,260 A | 1/1936 | Eustis et al. |
| 2,142,194 A | 1/1939 | Karfoil |
| 2,162,240 A | 6/1939 | Boldusoff |
| 2,646,622 A | 7/1953 | Christie et al. |
| 2,703,083 A | 3/1955 | Gross |
| 2,794,479 A | 6/1957 | Ganz |
| 2,823,672 A | 2/1958 | Schladermundt et al. |
| 2,862,846 A | 12/1958 | Blackford et al. |
| 3,309,274 A * | 3/1967 | Brilliant ........................ 424/9.6 |
| 3,754,332 A | 8/1973 | Warren |
| 3,802,445 A | 4/1974 | Wesley |
| 3,860,013 A | 1/1975 | Czapor |
| 3,869,555 A | 3/1975 | Heonis |
| 4,162,687 A | 7/1979 | Lorch |
| 4,270,556 A | 6/1981 | McAllister |
| 4,315,516 A | 2/1982 | Zappel |
| 4,315,517 A | 2/1982 | Krag |
| 4,550,741 A | 11/1985 | Krag |
| 4,776,358 A | 10/1988 | Lorch |
| 4,807,752 A | 2/1989 | Chodorow |
| 4,836,227 A * | 6/1989 | Charatan ...................... 132/324 |

(Continued)

FOREIGN PATENT DOCUMENTS

| | | |
|---|---|---|
| DE | 198 28 415 A1 | 1/1999 |
| DE | 101 18 944 A1 | 10/2002 |

(Continued)

OTHER PUBLICATIONS

Leonard G. Lorch, Safeguarded Flossing Device, Quintessence International, Apr. 1981, 415-416, vol. 12, No. 4, Quintessence Publishing Inc., Chicago, USA.

(Continued)

*Primary Examiner* — Robyn Doan
(74) *Attorney, Agent, or Firm* — Donn K. Harms

(57) ABSTRACT

A dental floss apparatus for cleaning the gaps between adjacent teeth which is comprised of a pair of handles that are configured for engagement with the fingers with strands of flossing substrate extending therebetween. The flossing substrates are spaced from each other, running substantially parallel and extending within an opening formed between the ends of the handles, with tension maintained by the user through employment of the handles. A dissolvable substrate is positioned within this opening through an engagement with one or both of the handles or the flossing substrate, and upon contact with the surface of the teeth, dissolves, and deposits a residue on the surface of the teeth and the surrounding area of the mouth. The dissolvable substrate may be formed of two substrate pieces with a central gap between them defining a means for targeting insertion of the substrate between adjacent teeth and may be colorized or fluorescent, and have an additive material such as mouthwash, breath freshener, cooling agent, or flavor.

17 Claims, 15 Drawing Sheets

U.S. PATENT DOCUMENTS

| | | | |
|---|---|---|---|
| 5,014,725 A * | 5/1991 | Patscot et al. | 132/324 |
| 5,033,488 A | 7/1991 | Curtis et al. | |
| 5,086,792 A | 2/1992 | Chodorow | |
| 5,209,251 A | 5/1993 | Curtis et al. | |
| 5,220,932 A | 6/1993 | Blass | |
| 5,226,435 A | 7/1993 | Suhonen et al. | |
| 5,357,990 A | 10/1994 | Suhonen et al. | |
| 5,407,623 A | 4/1995 | Zachariades et al. | |
| 5,479,952 A | 1/1996 | Zachariades et al. | |
| 5,518,012 A | 5/1996 | Dolan et al. | |
| 5,657,779 A | 8/1997 | Blass et al. | |
| 5,692,531 A | 12/1997 | Chodorow | |
| 5,800,823 A | 9/1998 | Blass | |
| 5,806,539 A | 9/1998 | Blass et al. | |
| 5,819,767 A | 10/1998 | Dix | |
| 5,819,768 A | 10/1998 | Bible et al. | |
| 5,897,895 A | 4/1999 | Bongiovanni | |
| 5,911,228 A | 6/1999 | Curtis et al. | |
| 5,973,290 A | 10/1999 | Noddin | |
| 6,080,481 A | 6/2000 | Ochs et al. | |
| 6,161,555 A | 12/2000 | Chen | |
| 6,220,256 B1 | 4/2001 | Dolan et al. | |
| 6,539,951 B2 | 4/2003 | Baillie et al. | |
| 6,552,024 B1 | 4/2003 | Chen et al. | |
| 6,596,298 B2 | 7/2003 | Leung et al. | |
| 6,604,534 B2 | 8/2003 | Hill | |
| 6,609,527 B2 | 8/2003 | Brown | |
| 6,656,493 B2 | 12/2003 | Dzija et al. | |
| 6,709,526 B1 | 3/2004 | Bailey et al. | |
| 6,740,332 B2 | 5/2004 | Zyck et al. | |
| 7,055,530 B2 | 6/2006 | Husted | |
| 7,281,541 B2 | 10/2007 | Lorch | |
| 7,537,450 B2 | 5/2009 | Karazivan | |
| 7,632,525 B2 | 12/2009 | Dodds et al. | |
| 7,678,397 B2 | 3/2010 | MacQuarrie | |
| 7,736,739 B2 | 6/2010 | Lutz et al. | |
| 7,740,020 B2 | 6/2010 | Lutz et al. | |
| 2003/0224090 A1 | 12/2003 | Pearce et al. | |
| 2003/0235630 A1 | 12/2003 | Nussen | |
| 2004/0036193 A1 | 2/2004 | Berry et al. | |
| 2004/0043134 A1 | 3/2004 | Corriveau et al. | |
| 2004/0048231 A1 | 3/2004 | Perlin | |
| 2004/0087467 A1 | 5/2004 | MacQuarrie | |
| 2008/0063325 A1 | 3/2008 | Miller et al. | |
| 2009/0117515 A1 | 5/2009 | Resk | |
| 2009/0120454 A1 | 5/2009 | Ochs et al. | |
| 2009/0120455 A1 | 5/2009 | Ochs et al. | |
| 2009/0142384 A1 | 6/2009 | Muller et al. | |
| 2009/0151747 A1 | 6/2009 | Bush | |
| 2009/0271936 A1 | 11/2009 | Walanski et al. | |
| 2010/0051051 A1 | 3/2010 | Hsu | |
| 2010/0076080 A1 | 3/2010 | Yelm et al. | |
| 2010/0086498 A1 | 4/2010 | Haught et al. | |
| 2010/0178252 A1 | 7/2010 | Sagel et al. | |
| 2010/0180912 A1 | 7/2010 | Ochs et al. | |
| 2010/0203467 A1 | 8/2010 | Karazivan | |
| 2010/0249831 A1 | 9/2010 | Vlasblom et al. | |
| 2010/0252063 A1 | 10/2010 | Grossman | |

FOREIGN PATENT DOCUMENTS

| | | |
|---|---|---|
| EP | 0 423 916 A1 | 4/1991 |
| EP | 1 033 145 A1 | 9/2000 |
| WO | PCT/GB00/02735 | 1/2001 |
| WO | PCT/US2004/016288 | 12/2004 |

OTHER PUBLICATIONS

Steven T. Bunn, How to Floss, drbunn.com, (c) 2000-2004 Last updated May 22, 2004, drbunn.com/flossing.htm, Steven T. Bunn, D.D.S., Alexandria, USA.

Leonard Lorch, Instructions on Awesome Floss (R.T.M.) dental floss, Awesome Floss (R.T.M.) dental floss, (c) 2009 Leonard Lorch, Leonard G. Lorch, San Rafael, USA.

Leonard Lorch, How to use Awesome Floss (R.T.M.) dental floss, Awesome Floss (R.T.M.) dental floss, (c) 2010 Leonard Lorch, Leonard G. Lorch, San Rafael, USA.

* cited by examiner

DENTAL FLOSS

BACKGROUND OF THE INVENTION

1. Field of the Invention

The present invention relates to an improved dental flossing apparatus. More particularly it relates to a flossing device and method which is easier and more comfortable to employ than conventional floss products and additionally provides a means to induce increased use through the provision of a gustatory sensation during use as means to encourage regular flossing by the user as part of an ongoing dental hygiene regime.

2. Prior Art

Virtually all dental health practitioners and professionals of the like recommend the use of dental floss for the removal of interdental plaque and particulate from between teeth and under the gum line. These are places that a toothbrush cannot reach and are common initiation sites for tooth decay and gum disease when not cleaned regularly and properly.

Conventional threadlike floss maintains many discouraging aspects to a new or ill-practiced user. It is often difficult to pass the round threadlike floss in between two adjacent teeth due to the resistance encountered by the tooth's side edges. Similarly, children as well as many adults find it hard to hold the distal ends of the floss which can painfully 'strangle' the fingers around which they are wrapped during use.

Furthermore, the conventional flossing regimen does not provide any initial or immediate positive reinforcement to the floss trainee other than of course any oral encouragement from an instructor. As a result, there is an inherent tendency of individuals, to reduce their flossing time and possibly halt any and all flossing regimens which the individual may have, with good intentions, initiated. Even in dedicated users having a flossing regimen, such a lack of encouragement or an inducement to continue, can be a resulting cause of reduced flossing over time. Attempts to solve some of these shortcomings and flaws have been attempted as is shown in prior art.

U.S. Pat. No. 7,281,541 to Lorch, while a definite improvement in the realm of flossing, teaches dental floss comprised of a planar flossing substrate with one or a plurality of apertures formed therein. About each aperture is a pair of edible substrate portions slightly larger than the aperture and joined together through the aperture in the substrate thereby securing it to the latter. In use the edible substrate that is flavored and/or impregnated with medicine, is dissolved or temporarily imparted onto the tooth giving the user a temporary flavor or visual stimulus providing positive reinforcement of the procedure. However, in some individuals, the engagement of the edible substrate to the planar substrate may impart a difficulty in the insertion of the floss to translatably engage in between two adjacent teeth. Surprisingly this is due to the added thickness of the initially blocking, not just dissolving, edible substrate.

As such, there is a continuing and unmet need for an improved device that when employed for flossing, immediately provides an easy and comfortable means to do so, while concurrently freshening breath during flossing and increasing the effectiveness of such a flossing session. The device should be easy to grasp in the user's fingers without numerous wraps therearound as is required of floss dispensed from containers. It should provide finger engageable ends to not only assist in positioning the floss in the user's mouth, but also to aid in the user engaging in easy employment of the proper flossing techniques and procedures set forth by a dental professional. Further, the device should provide a gustatory inducement to employ, and continue to use floss in an ongoing manner to users.

SUMMARY OF THE INVENTION

The device herein disclosed and described achieves the above-mentioned goals in surmounting the shortcomings of prior art. In a preferred mode, the device accomplishes this object through the provision of one or a plurality of any conventional commercially available waxed or unwaxed flossing substrates extending between two planar grips or handles. In a second, less preferred mode of the device, an aperture formed within a planar flossing substrate is provided also with two handles.

The device employs a first and second surface and a first and second end each engaged with a handle. The second end of the device is substantially a mirror of the first end. The flossing substrate extends between and connects the handles at a substantially central location thereon. These handles provide for engagement to the hand through compression between the thumb and one finger thereby eliminating the conventional need to wind the distal end of the flossing substrate about one's finger which frequently results in a strangulation of a user's fingers. The finger engageable handles are most preferably, a flexible hypoallergenic adhesive cloth tape commercially available as listed product number 1538 as manufactured by the 3M Company.

In a particularly preferred mode of the device, the flossing substrate is substantially planar in construction and made of expanded polytetrafluoroethylene (ePTFE). In other preferred modes of the device, the substrate may be multi-filament nylon or non-elastic ultra high molecular weight polyethylene (UHMWPE) or the like. Of course those skilled in the art will realize that other materials may be employed for the substrate and new materials adapted for such may come available. As such, any materials one skilled in the art might employ for the substrate are considered within the scope of this application.

In preferred modes of the disclosed device, a first and a second planar edible and dissolvable substrate are engaged at or near an innermost edge of the first and second handle by an engagement means, and both dissolvable substrates extend from this attachment end to a distal end a distance from the edge of the respective handle.

The edible substrate may be a pullulan or gelatin base. A pullulan substrate provides a fairly rapid rate of dissolution while a gelatin-based substrate dissolves less quickly and may be desired as well for that reason so as to allow more time for flossing while concurrently communicating a taste and/or cooling sensation to the user during the continued flossing session.

Both edible substrates extend to distal ends spaced from their engagement ends to handles, to a predetermined distance. The two edible substrates cover the flossing substrate extending to connections with the edges of both handles and which determine the distance between the two respective edges of the handles.

In a particularly preferred mode of the device, the edible substrates extend inward from their attachment to the innermost edges of the first and second handles a combined distance that is shorter than the length of the flossing substrate connecting the two handles. This forms a gap between the two opposing distal edges of the first and second edible substrates exposing the flossing substrate therein.

Preferably, the dissolvable edible substrate should be of a vertical width substantially equal to the width of the handles.

This maximizes the size of the edible substrate and therefor the time in the mouth required for a total dissolving. The larger size thus provides more time for flossing while concurrently providing the user with encouragement through communicated flavor, cooling agent, medicine or the like. The easy access to the floss therebetween maintains the engagability of the floss substrate between the user's teeth and the subsequent maneuverability within the mouth.

The gap created between the two distal ends of the edible substrate and exposing the flossing substrate, defines an engagement zone in which a saliva-coated tooth or pair of adjacent teeth can engage the flossing substrate without blocking interference from the edible substrate. In use, the flossing substrate is positioned within the space between any two adjacent teeth of a user and the engagement zone provides a means to see the underlying flossing substrate as well as some clearance for the edible substrate during flossing. As flossing commences the edible substrate, situated on both sides of the dental arch, proceeds to dissolve and deliver to the user the desired flavor, cooling agent, medicine, or the like as dictated by the choice of edible substrates. Since edible substrates are positioned on both sides of the gap, and hence both sides of the dental arch during any flossing session, flavor and/or medicine are adequately delivered to all saliva coated teeth and/or saliva coated gum tissue.

In another particularly preferred mode the edible substrates may extend further to a shared abutted edge centrally located on the device. Similarly, the edible substrates may extend even further and overlap about a central position on the device. For both modes, the abutted edge or overlap, the dissolving edible substrates will last longer due to size and might be preferable when used by novice flossers, or by individuals who floss for longer durations. While the underlying flossing substrate may not be initially visible since the gap is eliminated, engagement between the teeth is relatively simple since the distal ends of the edible floss are simply deflected by the teeth upon engagement of the teeth.

In still another particularly preferred mode one or a plurality of portions of edible substrate may be engaged on both surfaces of the device at or near the inner most edge of the handles. In this mode, the opposing layers of the edible substrates extending from the edges of each handle, cover and in effect sandwich the flossing substrate therebetween. As in the longer edible substrate mode, the addition of more edible substrate layers can provide an extended release of flavor, cooling agent, medicine, or breath freshening means as desired by a user or dental health professional. Furthermore, predetermined doses of medicine or the like can be employed on the device as dictated by the amount of edible substrate present on the device. Thus, the device can simultaneously provide a prescribed dose of medicine while promoting proper and continued flossing practice.

With respect to the above description, before explaining at least one preferred embodiment of the herein disclosed invention in detail, it is to be understood that the invention is not limited in its application to the details of construction and to the arrangement of the components in the following description or illustrated in the drawings. The invention herein described is capable of other embodiments and of being practiced and carried out in various ways which will be obvious to those skilled in the art. Also, it is to be understood that the phraseology and terminology employed herein are for the purpose of description and should not be regarded as limiting.

As such, those skilled in the art will appreciate that the conception upon which this disclosure is based may readily be utilized as a basis for designing of other oral hygiene structures, methods and systems for carrying out the several purposes of the present disclosed device. It is important, therefore, that the claims be regarded as including such equivalent construction and methodology insofar as they do not depart from the spirit and scope of the present invention.

It is an object of the invention to provide a dental flossing device that provides a gustatory means to encourage a flossing regime through the provision of an edible substrate.

It is another object of the invention to provide such an edible substrate with flavor, cooling agent, medicine, breath freshening means, or combinations thereof.

It is a further object of the invention to provide a dental device that is easy and comfortable to use for new as well as proficient floss users as well as easy to maneuver in the mouth.

Yet another object of the invention is to provide an engagement zone or gap to define a target to thereby guide a user to the correct position of the device for proper usage.

A further object of the invention is to provide one or a plurality of flossing substrates extending between two handles for use with both the upper and lower set of teeth.

Yet another object of the present invention is the provision of a plurality of any pre-existing commercially available waxed or unwaxed flossing substrate engaged between two handles.

Still a further object of the invention is to provide a neat and convenient packaging for single use employment of the device in a clean, moisture proof or sterile environment.

A further object of the present invention is to provide a dental device which is easy to manufacture and commercialize by pre-existing dental floss manufacturers and marketers and retailers of global-branded floss products to better serve end users.

Further objects of the invention will be brought out in the following part of the specification, wherein detailed description is for the purpose of fully disclosing the invention without placing limitations thereon.

BRIEF DESCRIPTION OF DRAWING FIGURES

FIG. 10b shows a side view of the device from FIG. 10a.

FIG. 11b shows a side view of the device from FIG. 11a.

DETAILED DESCRIPTION OF THE PREFERRED EMBODIMENTS OF THE INVENTION

Figure 1A:
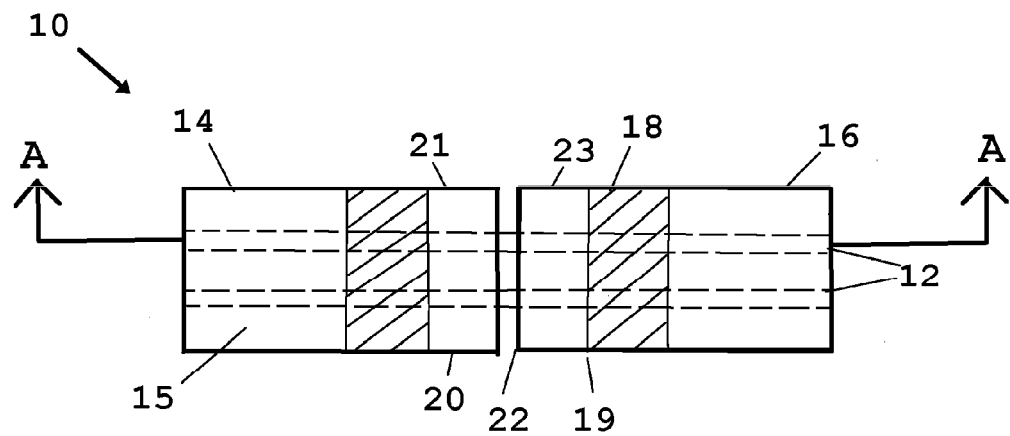
FIG. 1a shows a top plan view of a particularly preferred mode of the device showing a side surface and a gap.

Now referring to drawings in FIGS. 1-16, wherein similar components are identified by like reference numerals, there is seen in FIG. 1a a particularly preferred mode of the device 10. In this mode a left and right handle 14 and 16 are shown engaged to flossing substrate 12 communicating therebetween and providing means for engagement with the fingers of a user during use.

Also extending from an attachment point to each handle 14 and 16, from the same respective edge thereof where the flossing substrate 12 extends, are a first portion 21 and second portion 23 of a dissolvable and edible substrate 20 material which is adapted to dissolve when contacted by saliva coated teeth and gums. The edible substrate 20 portions 21 and 23, are sized to extend from their attachment point to their respective handle 14 and 16, a distance less than the total length of the flossing substrate 12 extending therebetween. Consequently when the handles 14 and 16 are engaged by the figures of a user in the as-used position (FIGS. 13 and 16), and the flossing substrate 12 is taught, a gap 25 is centrally located between the terminating ends of the first portion 21 and second portion 23 of the edible substrate 20 which defines an engagement zone 22 for the device 10. The engagement zone 22 provides a clearance and a visual targeting means for a user to properly position the device 10 to engage the flossing substrate 12 in the space between two adjacent teeth when a user is employing the device 10 in the as-used position to clean their teeth in a flossing procedure.

The sizing of the portions of the flavored edible substrate 20 and forming the length of the flossing substrate 12 to form the gap 25 and engagement zone 22, thereby provides users a targeting means and is particularly preferred. The targeting means so formed allows users an easy means to visually ascertain the proper positioning of the device 10 and flossing substrate 12 when held by the handles 14 and 16, to properly engage and employ it in a flossing session. Colorizing the edible substrate 20 provided a means to increase the ability of the user to see the gap 25 and the engagement zone 22 since the gap 25 will be void of the color. As such, providing colored edible substrate 20 will even allow users requiring glasses or contacts for close viewing to ascertain the proper position for engagement of the device 10 with their teeth, without their eyewear. For instance using a color or dye that fluoresces under room light or is otherwise bright, will cause the gap 25 to visually stand out against the two adjacent portions 21 and 23, of the edible substrate 20.

Those skilled in the art will realize that the employment of flossing substrate 12 in the proper length between the handles 14 and 16 to form the gap 25 along with the appropriately sized edible substrate portions 21 and 23 of the edible substrate 20, may be engaged to the handles 14 and 16 in any number of fashions, and all such means of engagement as would so occur, are considered to be within the scope of this application.

Figure 1B:
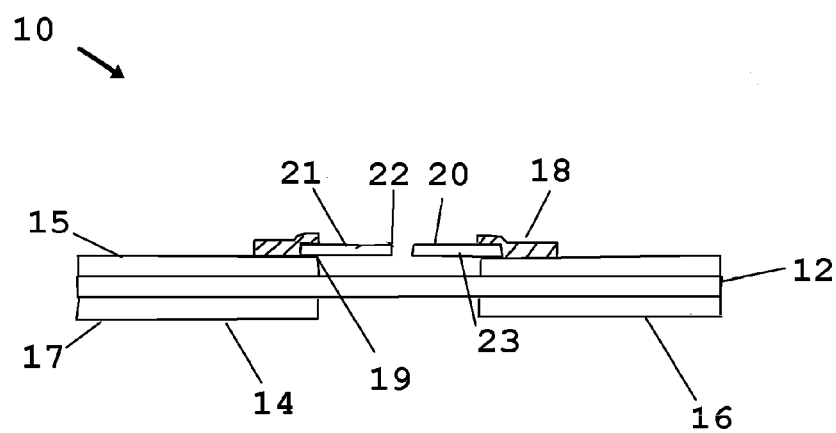
FIG. 1b shows a cross-sectional view of the device of FIG. 1a as seen along line AA.

One preferred mode of such attachment is shown in FIGS. 1a-1b, where the handles 14 and 16 are depicted with top and bottom planar surfaces 15,17 of a flexible hypoallergenic material. This hypoallergenic material has a tackified adhesive backing on adhesive cloth tape such as commercially available product number 1538 from the 3M Company.

One, or more preferably a plurality of flossing substrates 12, sized to form the gap 25, extend between respective engagements to each of the handles. A particularly preferred means to engage the flossing substrate 12 to the handles 14 and 16, is by sandwiching the substrate 12 between the inner surfaces of the top and bottom planar portions 15,17 of the handles 14,16. The top and bottom portions would be engaged using adhesive, sonic welding, molding, or other means to engage them in a manner to hold the flossing substrate 12 engaged therebetween.

As noted, a particularly preferred mode of the device 10 in all depicted modes, employs a plurality of flossing substrates 12 shown as two flossing substrates 12. Particularly preferred for ease of insertion between teeth, is a planar flossing substrate material formed of a shred-proof friction-lessening material such as expanded polytetrafluoroethylene (ePTFE). Alternatively, the device 10 may employ flossing substrate portions formed of multi filament nylon or a non-elastic ultra high molecular weight polyethylene (UHMWPE). The flossing substrate employing ePTFE, or nylon, or UHMWPE may be waxed or unwaxed flossing substrates.

The two sections of flossing substrate 12 employed on the device 10 may be similar in construction, or may employ different substrate types as desired by a user. However, due to the superior coverage a plurality of flossing substrates 12 provides during translation over the surface of teeth during flossing, the provision of at least two flossing elements 12 is desirable so as to aid a user in properly removing undesirable material from the surfaces of teeth being flossed.

A view from cross-sectional cut AA of FIG. 1a is seen in FIG. 1b. Edible and preferably flavored substrate 20 portions, suitable for dissolution in liquid and especially saliva, are shown as a first and second portion respectively 21, and 23 which extend from respective engagement to handles 14 and 16 to respective distal ends within an opening 11 formed in between the handles 14 and 16. The gap 25 formed between the distal ends of the first and second portions 21 and 23, as depicted, is sized smaller than the opening 11 between the handles 14 and 16 and thereby defines the engagement zone 22 for a user at a central portion of the opening 11. In one particularly preferred manner for all modes of the device 10 the edible substrate 20 is pullulan based to provide a means for rapid dissolution in the mouth during use. Also, the substrates 20 are formed in substantially rectangular shape. However, those skilled in the art can appreciate a multitude of shapes and forms that can be employed which achieve the same goal and are anticipated by this application.

The edible substrate portions 21,23 are shown on the first or top planar surface 15 of the device 10 at or near the innermost edges 19 of the handles 14,16 where the flossing substrate 12 communicates therebetween. As noted, a means for engagement of the edible substrate 20 may be achieved through the provision of secondary adhesive cloth tape 18, shown by hatched fill lines in the figure, engaging the substrate 20 to the first or top planar surface 15 at or near the innermost edge 19 of the respective handles. Of course other means for engagement for the edible substrate 20 may be employed and any such means of engagement as would occur to those skilled in the art is anticipated within the scope of this patent.

So engaged using adhesive or other means of engagement, the first and second portions 21,23 of the edible substrate 20 extend inward along one side surface of the flossing substrate 12 which communicates between the engaged handles. As noted, shown in a particularly preferred mode, are the edible substrate 20 portions extending to distal ends insofar as to maintain the gap 25 centrally located on the device 10 in the as-used position with the flossing substrates 12 taught between the handles, and thereby defining the engagement zone 22.

Figure 2:
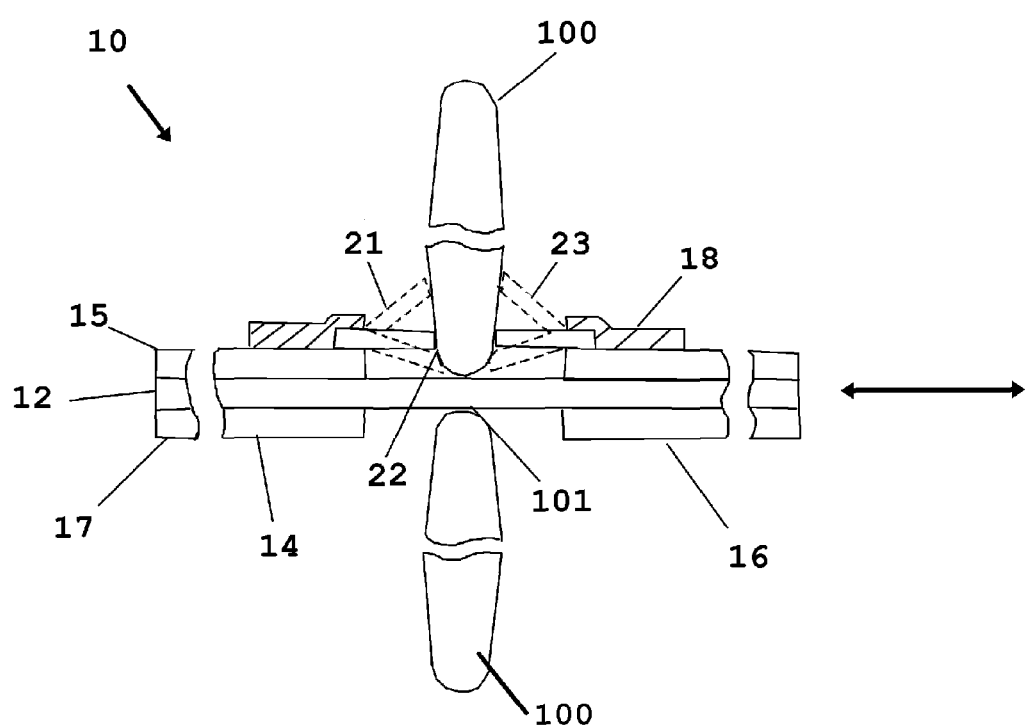
FIG. 2 is a top view of the device of FIG. 1a depicted in an as-used position wherein it is engaged in a space between two adjacent incisors.

This clearance is shown in FIG. 2 which depicts a top cross-sectional view of the device 10 in an as-used position. The device 10 is shown with the flossing substrate 12 engaged within the gap 101 between two adjacent incisors 100. The engagement zone 22 provides clearance for the first and second portions 21,23 of the edible substrate 20 from the adjacent incisors 100. Additionally the gap 24 defines a means for targeting the floss substrates 12 to a position proximate to the gap 101 between any two adjacent teeth of the user whereafter the floss substrates 12 may be slidably engaged into the gap 101 more easily.

Using conventional translational flossing motion, the edible substrate portions 21,23 are deflected by the incisors and as shown deflected by incisor 100. Concurrently the substrate portions 21 and 23 start to dissolve thereby depositing one or a combination of ingredients such as mouthwash, breath freshener, medicine, dye, cooling agent or flavoring into the mouth of the user and/or upon the saliva-coated teeth and gums. It may be desirable to employ a means to slow the rate of dissolution of the edible substrate portions 21 and 23 for slower flossing users such as children, and this may be accomplished in a number of ways known to those skilled in the art, for instance using a mixture of 76% gelatin base for the edible substrates 21 and 23.

Figure 3:
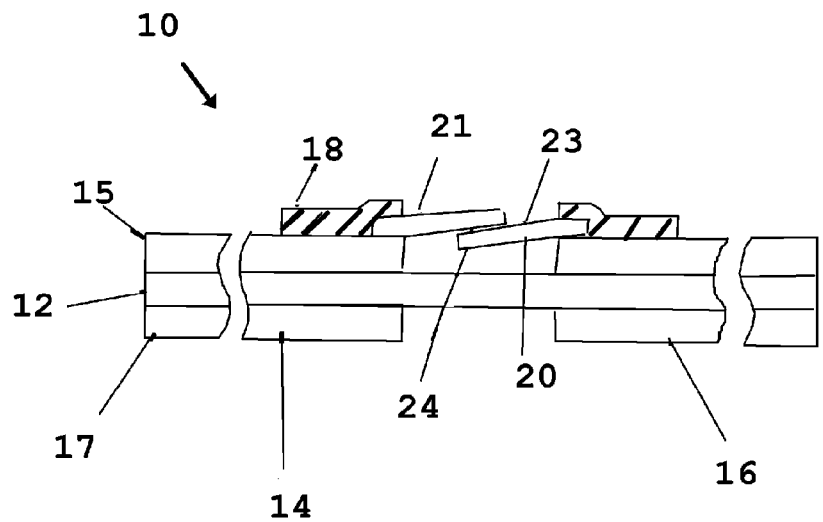
FIG. 3 shows a cross-sectional view of another particularly preferred mode of the device depicting an overlap of the edible substrates covering one side view of the gap and flossing substrate therein.

Another particularly preferred mode of the device 10 can be seen in the cross sectional view in FIG. 3. Similar to that of the mode described in FIGS. 1a and 1b, construction of device 10 employs an attachment of the handles 14 and 16 to the edible substrate 20 and the flossing substrate 12. In the depicted mode of the device 10 in FIG. 3, the first and second edible substrate portions 21,23 extend insofar as to create an overlap 24 of the first and second portions. This mode of the device 10 provides an increased portion of edible substrate 20 which can be deposited in the mouth of the user. Upon engagement of the flossing substrate 12 to a pair of adjacent teeth (not shown) the portions 21,23 are simply deflected away. While the preferred gap 25 is not provided for targeting, the overlap point of the substrate portions 21 and 23 may also be employed, or, the two substrate portions 21 and 23 may be formed of different colors to enhance the overlap as the targeting position for engagement to the teeth by the user.

Figure 4:
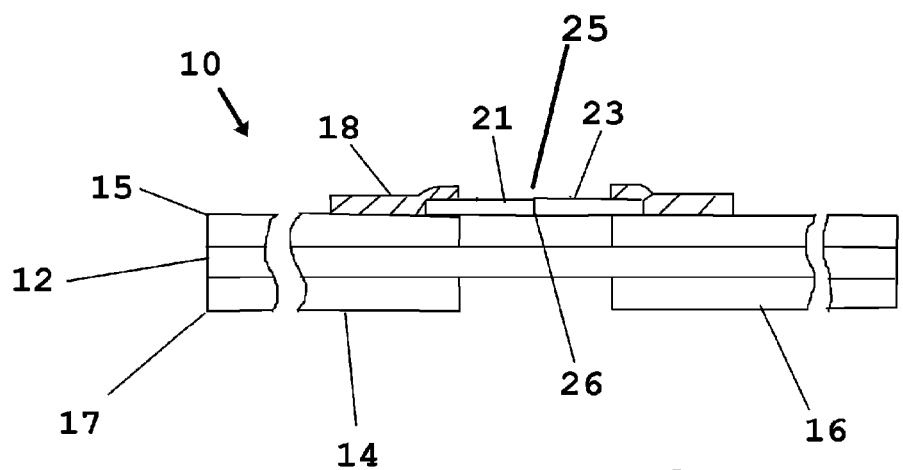
FIG. 4 shows a cross-sectional view of yet another particularly preferred mode of the device depicting the edible substrates extending inward to a shared abutment of their distal ends.

Yet another preferred mode of the device 10 is seen in a similar cross sectional view in FIG. 4. While similar in construction and use to the device of FIG. 1a and 1b, this mode of the device 10 employs the first and second edible substrate portions 21 and 23, having a length which provides for abutting distal ends 26 at the gap 25 which may be used for targeting at engagement with the user's teeth. The position of the gap 25 may be enhanced using different color substrate portions 21 and 23, or by terminating the colorizing of the substrate portions 21 and 23 just before their distal ends 26 thereby forming a virtual gap 25 viewable by the users for targeting the device 10 for insertion between their teeth during flossing.

Figure 5A:
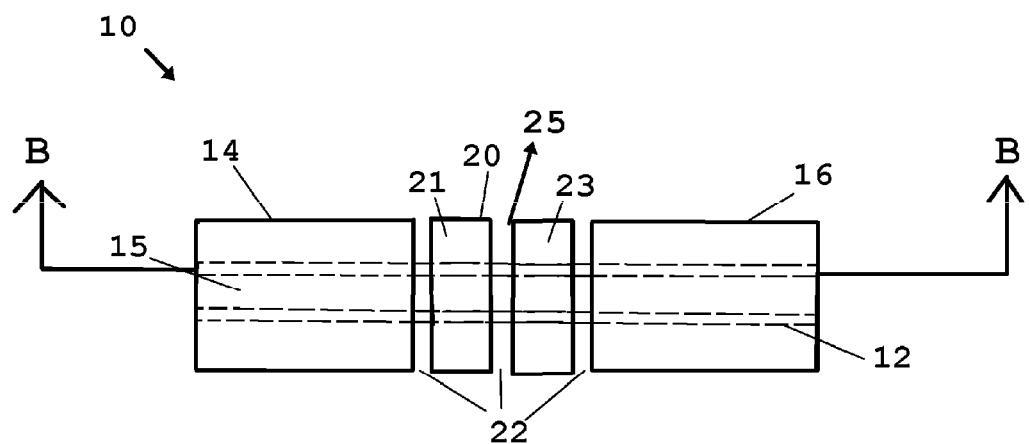
FIG. 5a is a top plan view of still another preferred mode of the disclosed device depicting edible substrates engaged on both surfaces of two flossing substrates with a plurality of engagement zones therein.
Figure 5B:
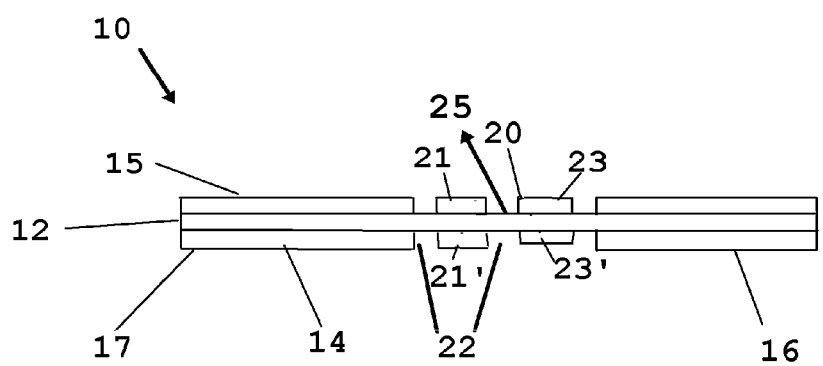
FIG. 5b is a side cross-sectional view of the device of FIG. 5a seen from line BB.

A further mode of the device 10 is shown in FIG. 5a and side cross-sectional view about line BB shown in FIG. 5b. Employing similar construction and means of engagement of the left and right handles 14,16 with the flossing substrate 12 as that of FIG. 1, this mode employs first and second substrates 21 and 23 in a sandwiched engagement with opposing first and second portions 21',23' of edible substrate 20, upon the flossing substrate 12. The first and second portions 21,23 shown in the view of the first or top planar surface 15 are respectively joined by an engagement means to the opposing first and second portions 21',23' of the second or bottom planar surface 17, thereby providing a means to hold them in place on the flossing substrate 12. Means to mate the portions of the top and bottoms surfaces may include one or a combination of edible adhesives or by simply wetting the substrates and allowing them to dry after applying contact pressure on the two portions. For the configuration shown in the figure a plurality of engagement zones 22 are created, and allow for a plurality of targeting or initiation positions to be employed by the user when engaging the flossing substrate 12 between teeth.

Figure 6A:
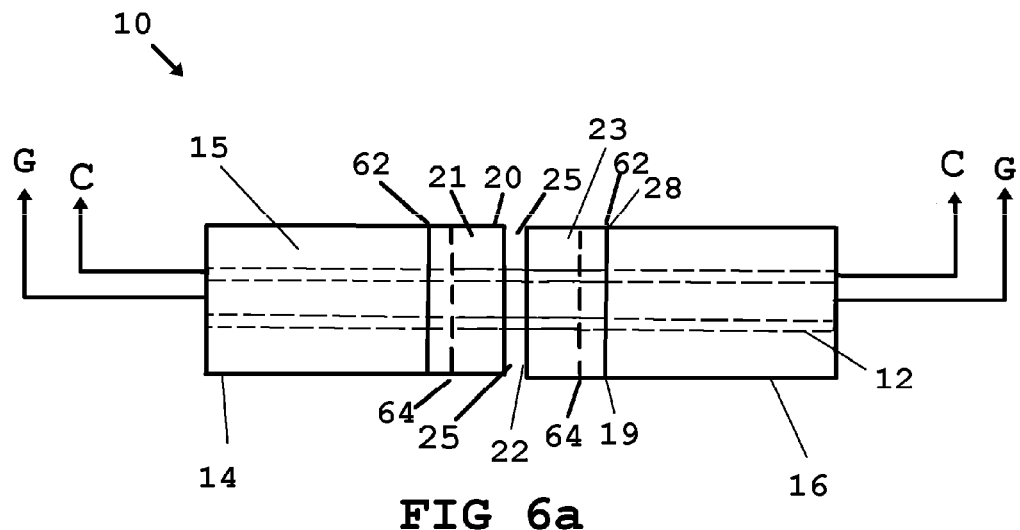
FIG. 6a depicts what is considered a current best mode of the device showing a top plan view and a layer of edible substrate extending from handles.
Figure 6B:
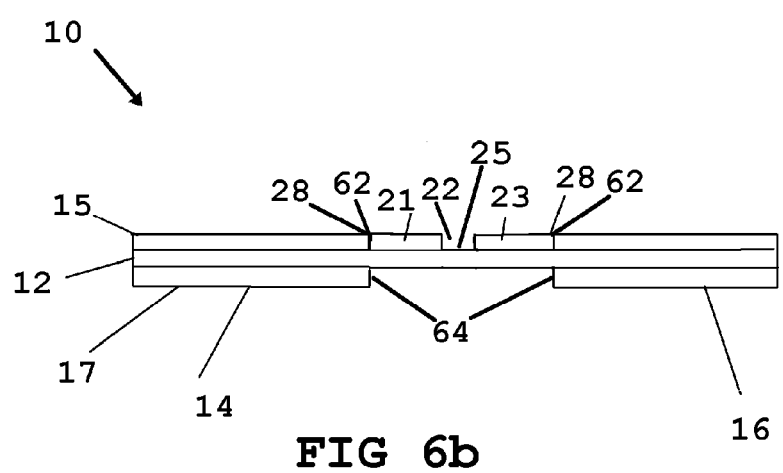
FIG. 6b shows a cross-sectional view of the device of FIG. 6a seen from line CC.
Figure 6C:
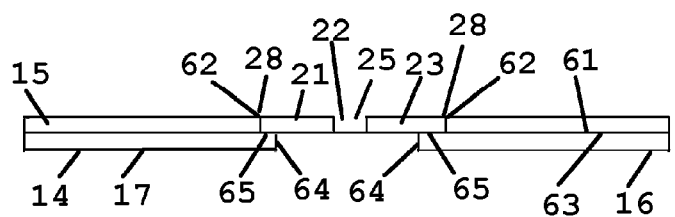
FIG. 6c depicts a cross-sectional view of the device along line G-G.

The best current mode and the most preferred mode of the device 10 is shown in FIGS. 6a, 6b and 6c. As evidenced from FIGS. 6a, 6b and 6c, the first or top planar surface 15 has, as shown in FIG. 6c, an inner most surface 61 and the second or bottom planar surface 17 has an inner most surface 63. As further evidenced in FIG. 6c, and therein on each handle 14 and 16, first and second portions 21, 23 of edible substrate 20 are engaged respectively on a ledge or an inner most portion 65 of the inner most surface 63 of the second or bottom planar surface 17 thereof, thereby joining the respective portions 21 and 23 of edible substrate 20 to handles 14, 16. As even further evidenced in FIGS. 6a, 6b and 6c, first and second portions 21, 23 of edible substrate 20 are engaged respectively on the handles 14 and 16 at the inner most edges 62 of the first or top planar surface of the handles 14 and 16 at the respective abutted edges 28 shared therebetween. As evidenced in FIG. 6c, each inner most edge 64 of the second or bottom planar surface 17 of each respective handle 14 and 16 is longitudinally spaced apart from the inner most edge 62 of the first or top planar surface 15 to form a ledge or an inner most portion 65 on an inner most surface 63, on each handle 14 and 16. As in the device of FIG. 1, a gap 25 defining a means for targeting or an engagement zone 22 is formed in a centrally located position on the device 10 providing the target for means of engagement of the device 10 for use. As shown in FIGS. 6a, 6b and 6c, the device 10 represents the best mode and the most preferred mode of the invention, and the device 10 represents the most efficient structure employing the least amount of the flexible and hypoallergenic tackified adhesive cloth tape and the like employed in the handles 14, 16.

Figure 7A:
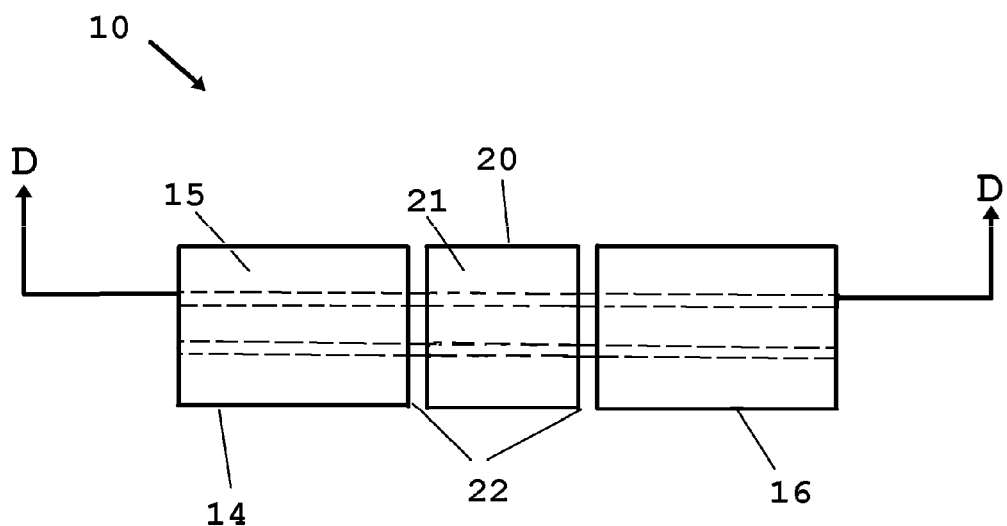
FIG. 7a is another preferred mode of the device depicting the edible floss engaged to the parallel flossing substrates communicating between two handles.
Figure 7B:
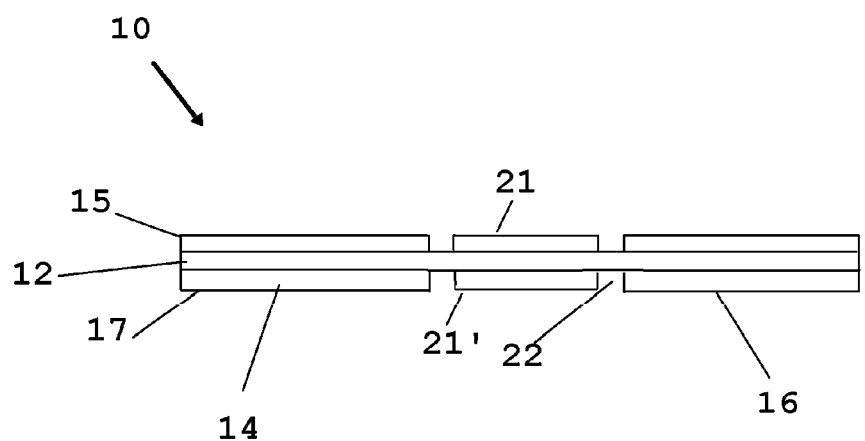
FIG. 7b shows a cross-sectional view of the device of FIG. 7a seen from line DD.

Still a further particularly preferred mode of the device is seen in FIGS. 7a and 7b. A substantially larger edible substrate 20 is engaged with a first portion 21 on the first or top planar surface 15 and a second portion 21' of edible substrate 20 is positioned on the second or bottom planar surface 17. The two portions of edible substrate 20 are held in place on the flossing substrate 12 by means of engagement such as adhesive or by engagement of the material forming the substrate portions. Gaps providing multiple engagement zones 22 for targeting during use are maintained near both the first and second handles 14, 16.

Figure 8A:
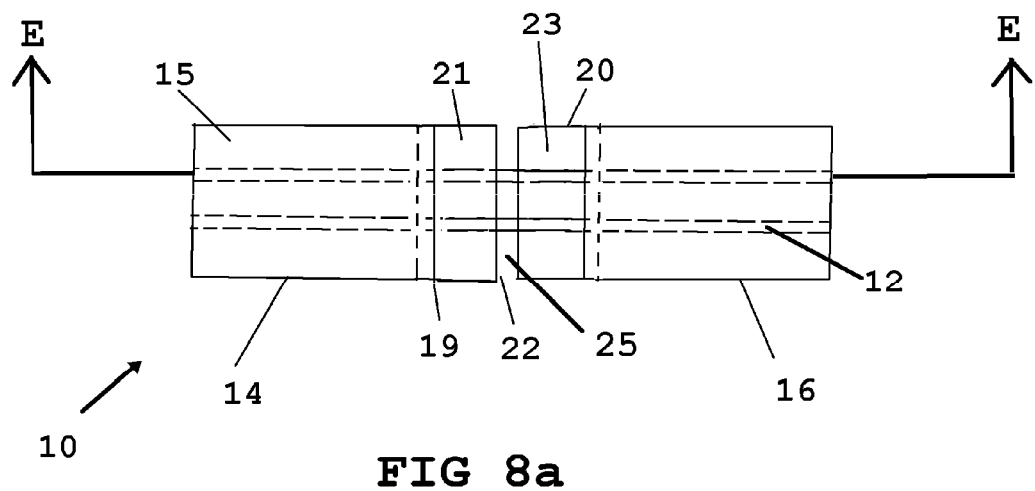
FIG. 8a is a further preferred mode of the device having multiple layers of edible substrate extending from an engagement to each handle on opposite sides of the floss.
Figure 8B:
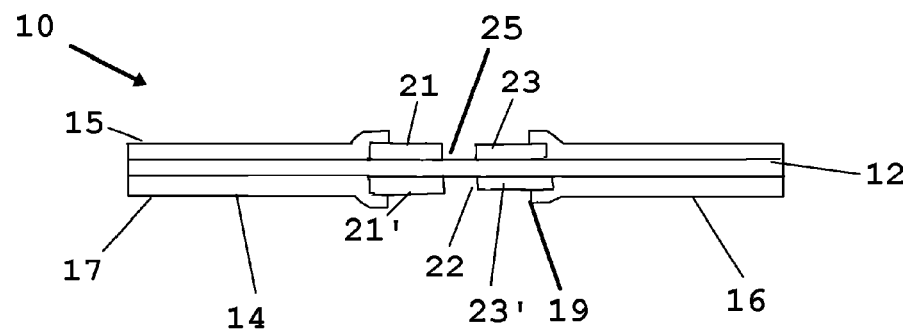
FIG. 8b shows a cross-sectional view of the device of FIG. 8a seen from line EE.

Another preferred mode of the device is shown in FIGS. 8a and 8b. In this mode first and second portions 21, 23 of edible substrate 20 on the top planar surface 15 and first and second portions 21', 23' of edible substrate on the bottom planar surface 17 are engaged to the respective handles 14, 16 at the inner most edge 19 by a surrounding means of engagement. Such an engagement means may be a substantial overlap at the edge 19 of the two opposing portions of material forming the handles themselves thereby adhering or engaging the edible substrate 20 in a manner for it to extend toward the opposite handle and over the flossing substrate 12. Again, a gap 25 forming the target or engagement zone 22 is maintained.

Figure 9A:
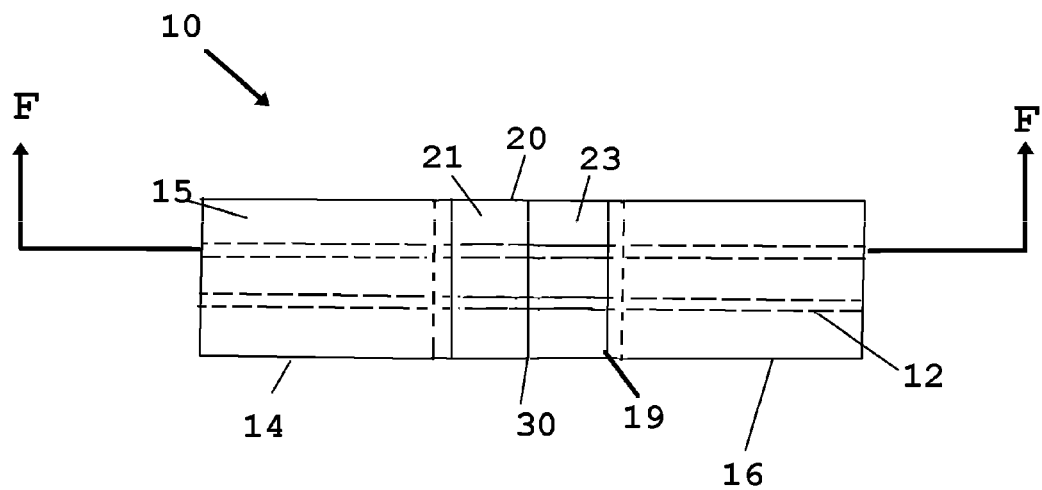
FIG. 9a shows another preferred mode of the device having multiple layers of an edible substrate which abut each other on opposite sides of the floss substrate.
Figure 9B:
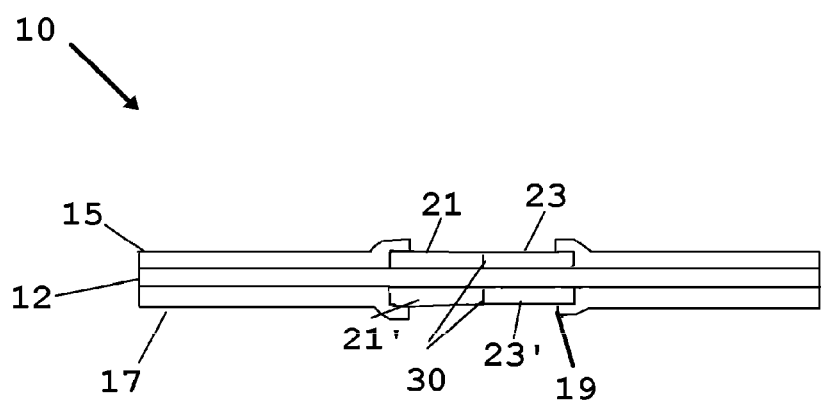
FIG. 9b shows a cross-sectional view of the device of FIG. 9a seen from line FF.

FIGS. 9a and 9b show still another mode of the device 10 similar to that of FIGS. 8a and 8b except that the first and second portions of edible substrate 20 of both the top and bottom surface 21, 23, 21', 23' extend toward respective opposite handles to respective abutted edges 30 forming the target defining an engagement zone for the user during use, as opposed to leaving the gap defining the engagement zone 22 previously described.

Figure 10A:
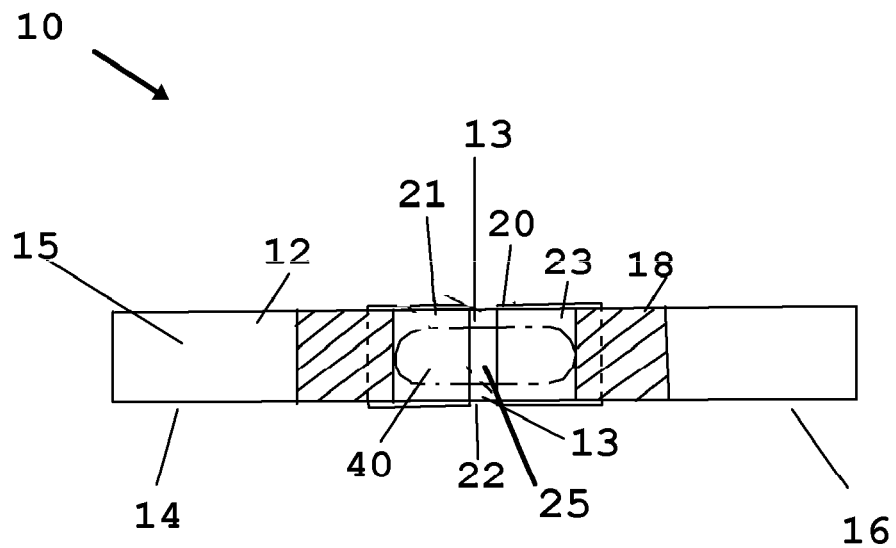
FIG. 10a is still another mode of the device.
Figure 10B:
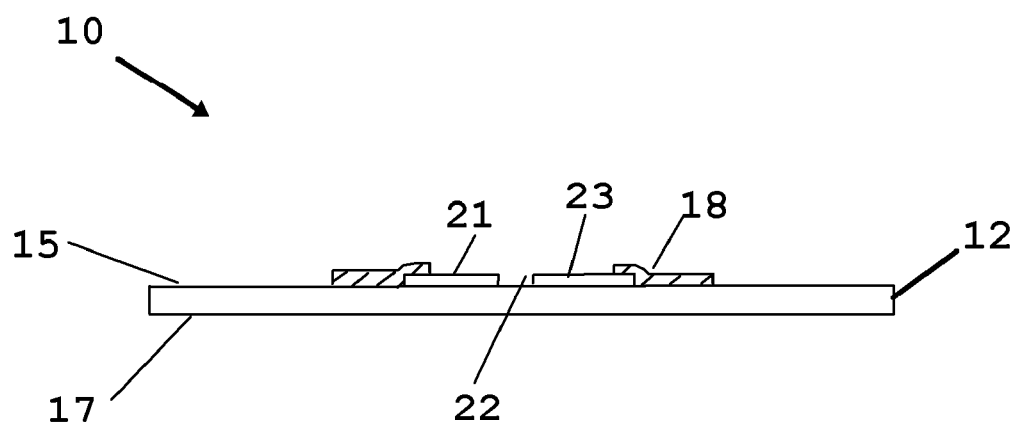

FIGS. 10a and 10b show an additional mode of the device 10 configured by a flossing substrate 12 with an aperture 40 formed communicating between the first or top planar surface 15 and a second or bottom planar surface 17. First and second handles 14, 16 are defined by end portions of the planar flossing substrate 12. Side portions 13 of the planar flossing substrate 12 extend around the perimeter of, and help define the aperture 40, and preferably align with the edge of the adjacent substrate 12 thereby providing an elongated means to floss when engaged within the crevices between teeth.

First and second portions 21, 23 of edible substrate 20 are engaged on one surface such as the first or top planar surface 15 of the device by operative means of engagement. Engaged to the flossing substrate 12, portions 21, 23 are cut or formed in a manner to overlap the aperture 40 and have the same side edge, that is widths, as the flossing substrate 12. The portions 21, 23 are engaged at or near the ends of the aperture 40 using means of engagement such as adhesive or tape 18. The portions 21, and 23 extend inward and over the aperture 40. The gap 25 is maintained between the two portions and defines the target for the user in the engagement zone 22 as previously described.

Figure 11A:
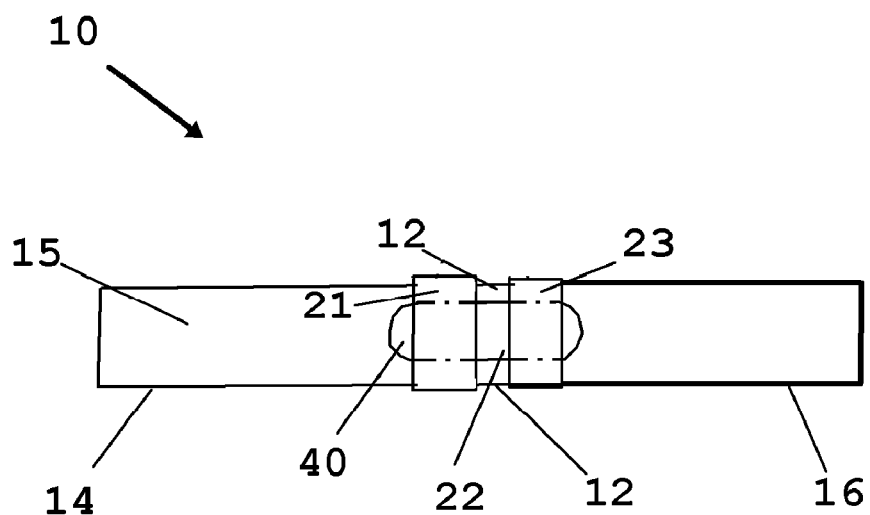
FIG. 11a shows another mode of the device.
Figure 11B:
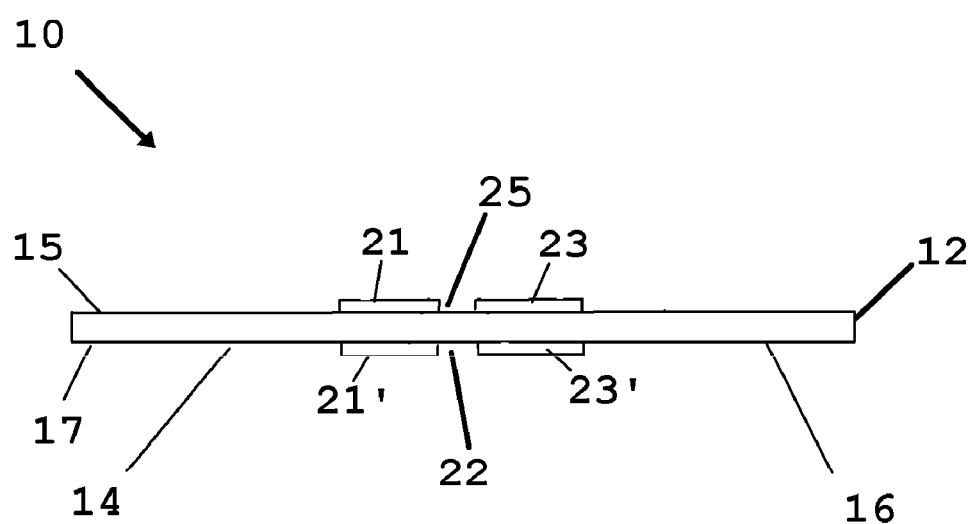

An additional mode of the device 10 is depicted in FIG. 11a and 11b. First and second portions 21, 23 of edible substrate 20 positioned on both the first or top planar surface 15 are respectively joined by an engagement means to the first and second portions 21', 23' on the opposing second or bottom planar surface 17 holding them in place over the aperture 40. Means to mate the portions of the top and bottoms surfaces may include one or a combination of edible adhesives or by simply wetting the substrates and allowing them to dry after applying contact pressure on the two portions.

Figure 12:
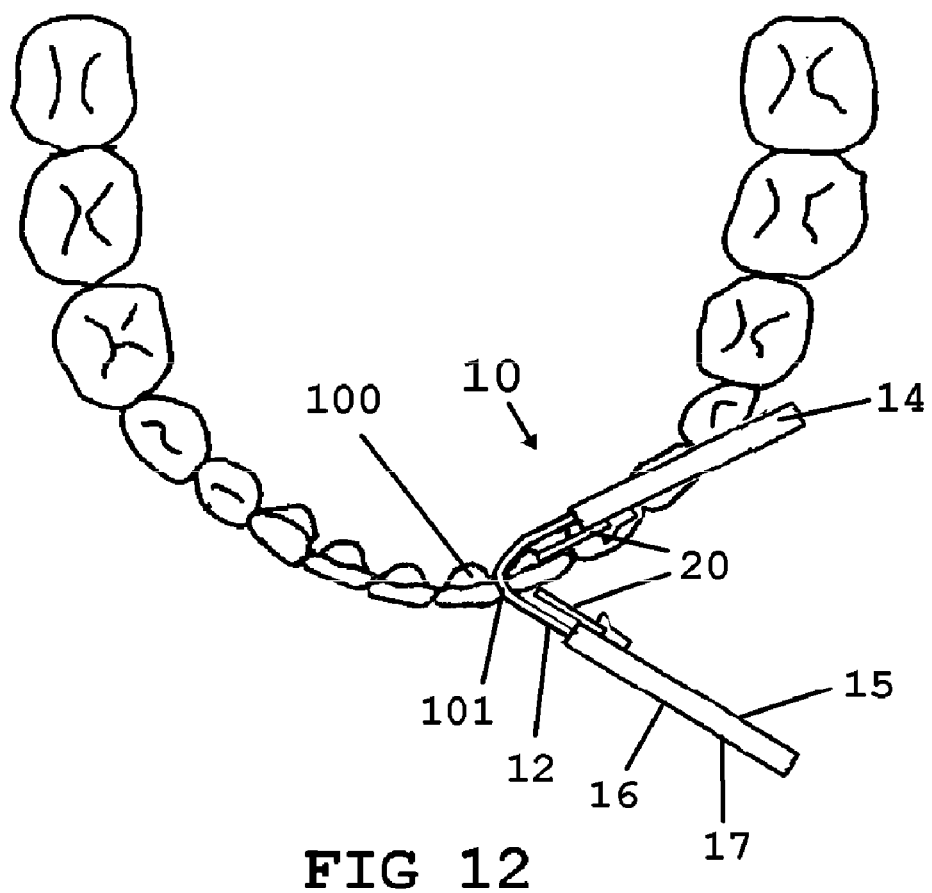
FIG. 12 is a top view of the device from FIG. 1a depicted in an as-used position between two adjacent teeth and shown translatably engaged within the space between a pair of incisors.

FIG. 12 shows a top view of the device 10 from FIGS. 1a and 1b in the as-used position translatably engaged for flossing. The flossing substrate 12 is shown engaged within the space 101 between two adjacent incisors 100. The edible substrate 20 is positioned near the incisor 100 and as contact with a saliva coated tooth or gum tissue begins, the substrate 20 proceeds to dissolve and deposit the flavor, cooling agent, medicine, etc. or combination thereof.

Figure 13:
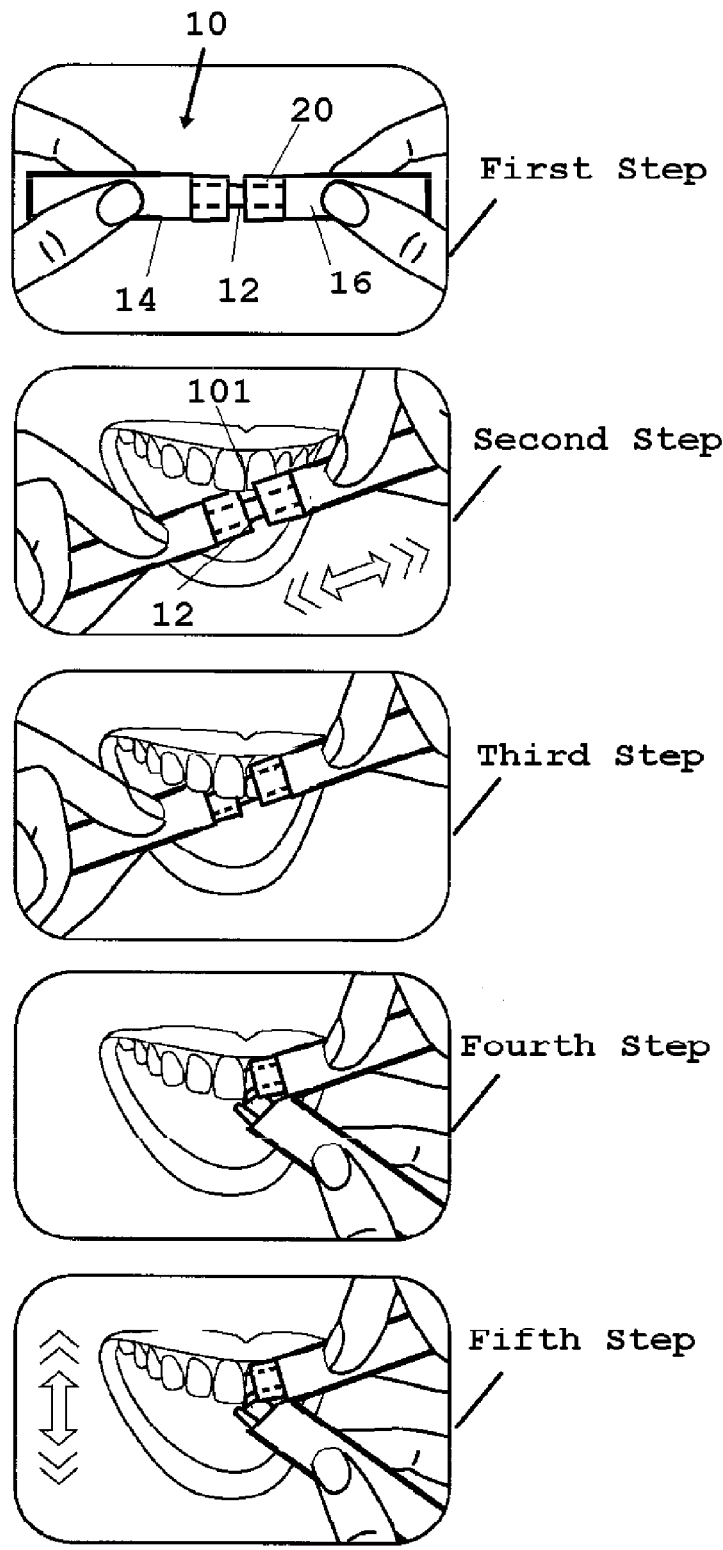
FIG. 13 shows a sequence of five steps for employment of the device with the mode of FIG. 1a as depicted.

More detailed depictions of the method of use associated with the device 10 may be seen in FIG. 13. The device 10 is grasped between the thumb and forefinger at the respective handles 14, 16. The user then engages the flossing substrate 12 within the engagement zone 22, overlap 24, or abutted edge 28, 30 of the edible substrate 20 to glide into the space 101 between two adjacent teeth 100. A flossing up and down motion, or reciprocating motion, then proceeds to cause a cleaning of the space between teeth while saliva upon the saliva coated teeth and/or gums, continually dissolves the edible substrate 20.

Figure 14:
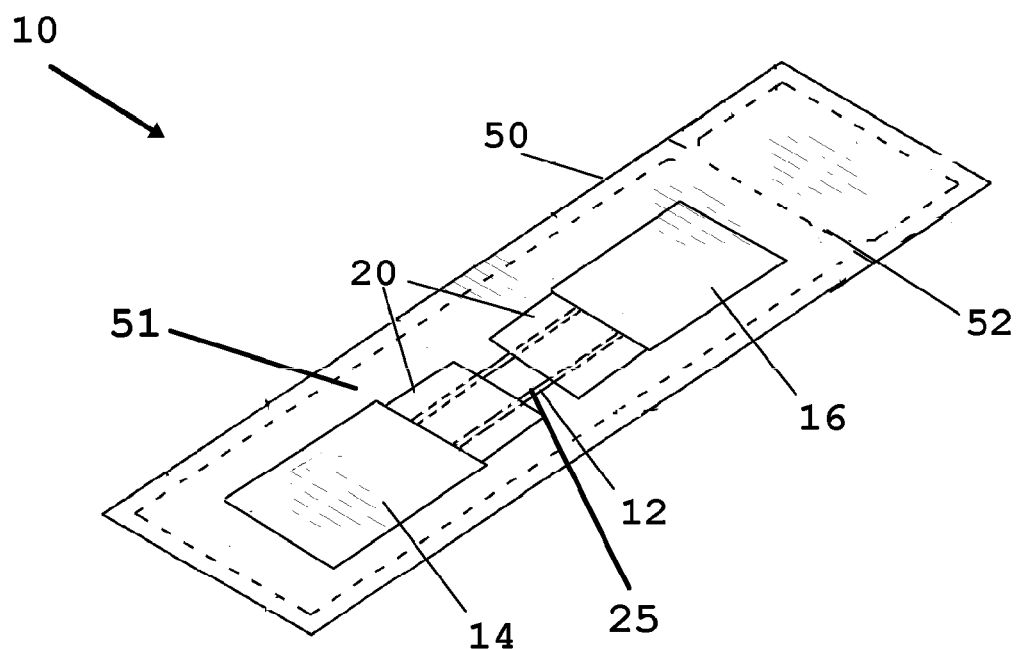
FIG. 14 is a perspective view of the device in a particularly preferred mode, wherein it is surrounded by a removable package forming a sterile storage compartment for the device therein.

In FIG. 14 there is shown a perspective view of the device 10 in a particularly preferred mode which would be employable in a portable but clean, moisture proof, and/or sterile fashion. This mode of the device 10 would be particularly adapted for being carried by the user during travel, or for dispensing by hotels and the like to patrons staying on the property much like soap and other toiletries. As depicted, the device 10, which could be any mode of the device 10 herein, is surrounded by a removable package 50 forming a clean, moisture proof and/or sterile storage compartment 51 for the device 10 therein. The package 50 is shown in transparent form, however it can also be opaque and may have indicia thereon showing the name of the hotel or dispensing entity. Further, the indicia may also include the depicted steps of FIG. 13 to educate users as to the proper manner to employ the device 10 once removed from the package 50.

In the mode of the device 10 in combination with the package 50 of FIG. 14, the device 10 is employed in a single use disposable manner. In a method of use, the user would hold the device 10 encased within the clean, moisture proof and/or sterile compartment 51 of the package 50 in their hands. In a next step, a tear off portion 52 would be removed to provide a means to access the device 10 within compartment 51 of the package 50. Thereafter the user would employ the device 10 in the method depicted in FIG. 13. Once finished the user would dispose of the device 10 and the package 50.

Such individual combinations of the device 10 and package 50 may be sold separately or in a container of many individual packages 50 which may be separated or may be on a roll of individually removable packages 50 with each containing a device 10 within their respective compartment 51. Sold and distributed in bulk, the device 10 would be especially adapted for use and individually dispensing, or sampling, to any global or domestic manufacturer or marketer of pre-existing globally branded or retail-store branded dental flosses, trade show booths and dental schools for dentists or dental hygienists, dental patients visiting the dentist or dental hygienist, medical patients visiting a medical doctor or dentist who prescribes regular flossing to minimize system-wide inflammation due to gum disease, guests in their hotel bathrooms, first class airline passengers, cruise ship passengers in their cabin bathrooms, astronauts, hospital patients, crew members in submarine bathrooms, elementary school teachers and/or elementary school students in their classrooms, women on the go carrying purses, men whose clothes have pockets, oral care companies and/or insurance companies who analogous to providing good driver discounts or discounts for exercise and/or prevention seek better compliance by dental patients monitored by dental or medical professionals, and other venues such as travel kits or inserts to or piggybacked on boxes of a global brand of toothpaste on the shelves of supermarket aisles where users may not yet have their own supply of floss with them, or where a one-use flossing component, or likeness of such a component and proper flossing instructions actually purchased in a virtual world created by residents (people like you) participating on the world wide web in games simulating real life such as the Second Life® game by Linden Research Inc. whose well known on-line games can also be a virtual way to encourage or train someone on a new flossing component virtually before they attempt the real thing in real life, would all be especially desirable when used for the first time or used regularly to help maintain, improve or help encourage the habit of improving oral health and system-wide health.

Figure 15A:
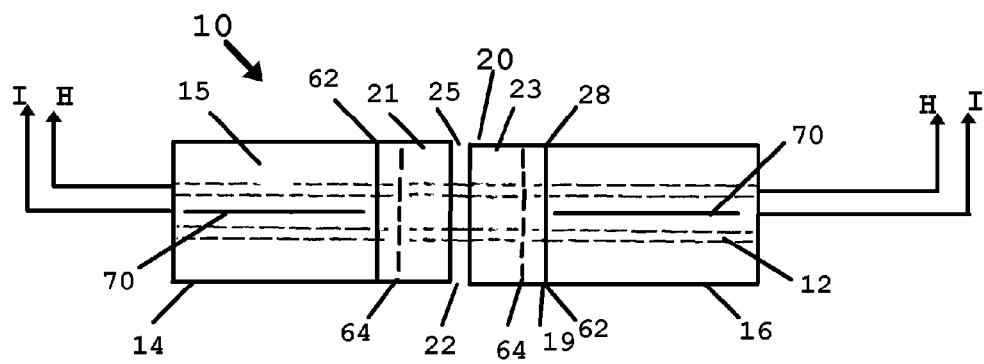
FIG. 15a is yet a further preferred mode of the device showing a top view and a layer of edible substrate extending from handles that each have a slit or aperture.
Figure 15B:
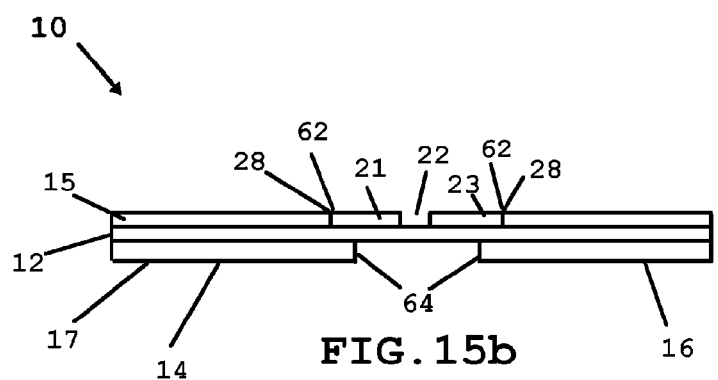
FIG. 15b shows a cross-sectional view of the device of FIG. 15a seen from line HH.
Figure 15C:
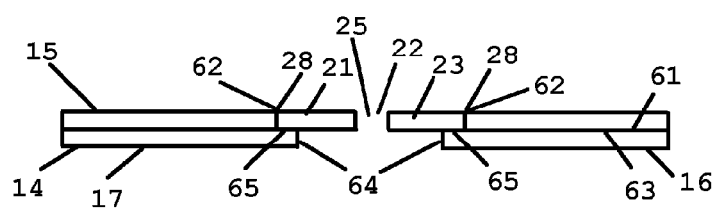
FIG. 15c shows a cross-sectional view of the device of FIG. 15a as seen from line II.

An alternate, and optional, embodiment of a particularly preferred mode of the device 10 is shown in FIGS. 15a, 15b and 15c. FIGS. 15a, 15b and 15c respectively show views of the device 10 similar to but further modified from FIGS. 6a, 6b and 6c. The structure of the device 10 from FIGS. 15a, 15b and 15c is identical to the structure of the device 10 in FIGS. 6a, 6b and 6c except for a transversely centered and longitudinally centered longitudinal slit or aperture 70 within each handle 14, 16 of device 10. In this particularly preferred mode of the device 10, each handle 14, 16 is dimensioned large enough so that each longitudinal slit or aperture 70 in each handle 14 and 16 is dimensioned large enough to be capable of being easily penetrated by a forefinger, and each handle 14 and 16 is dimensioned large enough to be capable of being held and tensed to a useful degree of tension between forefingers as occurs during an alternate kind of flossing session. Such a slit or aperture 70 in each handle 14, 16 of the device 10 can be incorporated to alternately, and optionally, modify the structure of any other mode of the invention.

Figure 16:
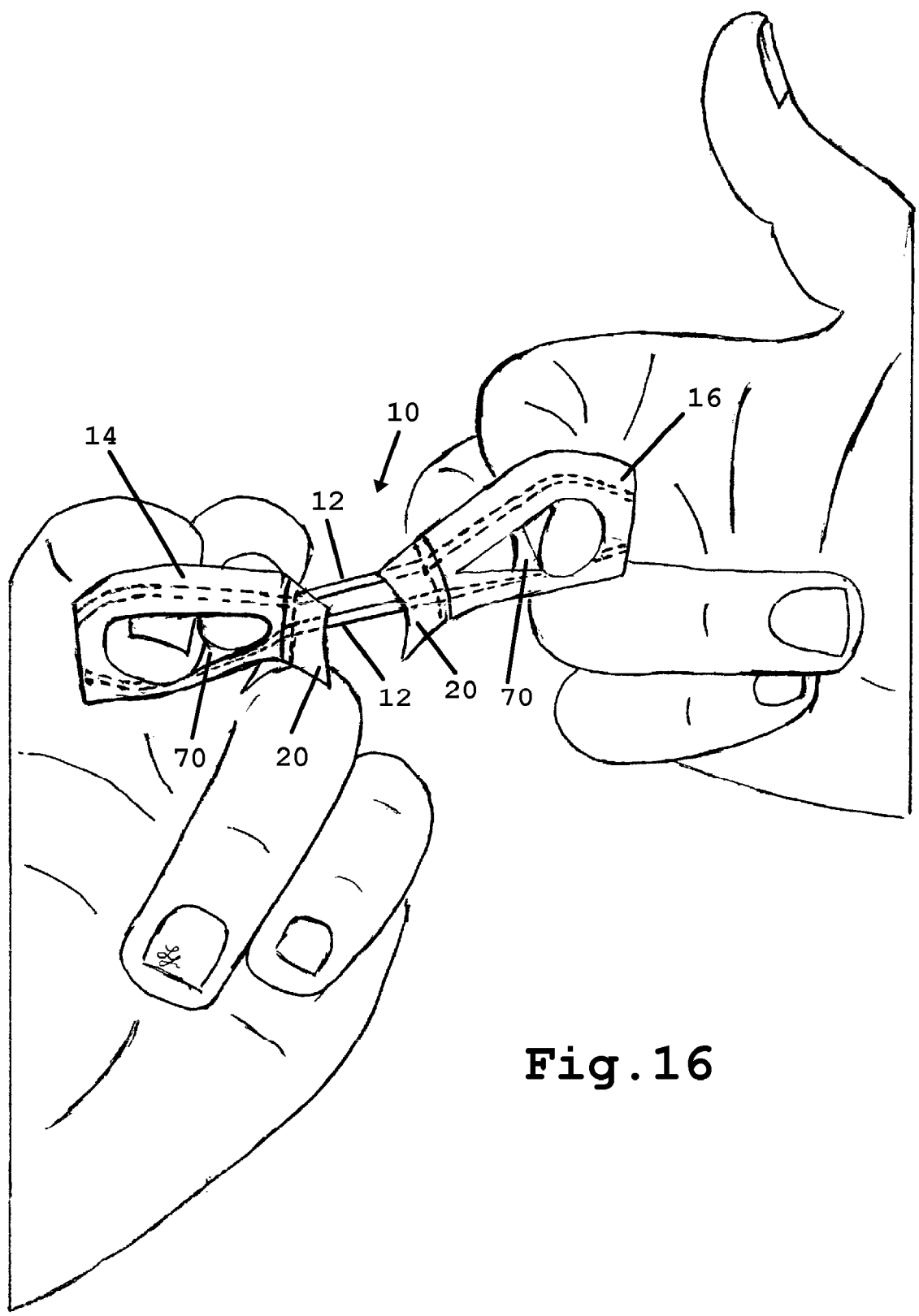
FIG. 16 shows, with the mode of FIG. 15a depicted, an alternate, and optional, preferred first step that may be substituted for the first step in the sequence of steps of FIG. 13 which may be further optionally modified, as not shown, for use of the device with the mode of FIG. 15a depicted.

FIG. 16 shows, with the mode of FIG. 15a depicted, an alternate, and optional, preferred first step that may be substituted for the first step in the sequence of steps of FIG. 13 which may be further optionally modified throughout, as not shown, for use of the device 10. FIG. 16 shows an easy way to hold the device 10 tensed between two forefingers and pressed by tips of two middle fingers at the ready.

Referring to the first step of the sequence of five steps for use of the device 10 depicted in FIG. 13, FIG. 16 shows an alternate, and optional, first step of the method of use of device 10 from FIG. 15 easily held and tensed by forefingers and pressed by tips of middle fingers at the ready to subsequently, and as not shown, with a forefinger in each longitudinal slit or aperture 70 of each handle 14 and 16 and with the tip of a middle finger on each handle 14 and 16, easily maneuver and use the device 10 to floss behind and between back teeth and/or between front teeth and anything in between.

While all of the fundamental characteristics and features of the improved flossing invention have been shown and described herein, with reference to particular embodiments thereof, a latitude of modification, various changes and substitutions are intended in the foregoing disclosure and it will be apparent that in some instances, some features of the invention may be employed without a corresponding use of other features without departing from the scope of the invention as set forth. It should also be understood that various substitutions, modifications, and variations may be made by those skilled in the art without departing from the spirit or scope of the invention. Consequently, all such modifications and variations and substitutions are included within the scope of the invention as defined by the following claims.

What is claimed is:

1. A dental floss apparatus for cleaning the gap between two adjacent teeth in the mouth of a user, comprising:
   a plurality of strands of flossing substrate extending between engagements with respective first ends of a pair of handles;
   said handles configured for engagement with the fingers of a user thereby providing means for said user to maintain said flossing substrate tensioned and extending within an opening formed between said respective first ends of said handles;
   said plurality of strands of flossing substrate while tensioned being spaced from each other a distance defining a void there between, and running substantially parallel;
   a dissolvable substrate positioned within said opening through an engagement with one of said handles or said flossing substrate;
   said dissolvable substrate formed of two substrate pieces each of said pieces extending from a respective said engagement, to respective distal ends;
   said distal ends defining opposing sides of a central gap sized smaller than said opening and positioned centrally in said opening;
   said dental floss apparatus having an as-used position, with said flossing substrate extending within said opening and concurrently positioned within said gap between two adjacent teeth;
   translation of said dental floss apparatus in said as-used position providing a respective translating contact of each of said plurality of strands of said flossing substrate with respective surfaces of said teeth; and
   a dissolving of said dissolvable substrate with said dental floss apparatus in said as-used position, depositing a residue on surface areas of said teeth and the surrounding mouth of said user.

2. The dental floss apparatus of claim 1, additionally comprising:
   said dissolvable substrate being colorized; and
   an enhanced contrast between said distal ends of said dissolvable substrate and said central gap therebetween providing a visually enhanced said means for targeting said flossing substrate.

3. The dental floss apparatus of claim 2 wherein said handles configured for engagement with the fingers of a user comprise:
   each of said pair of handles being substantially planar; and
   opposing surfaces on each of said pair of handles sized for a contact with one of a finger and a thumb of a user thereon in a frictional engagement thereto.

4. The dental floss apparatus of claim 3, additionally comprising:
   said dissolvable substrate having one or a combination of additive materials from a group consisting of mouthwash, breath freshener, cooling agent and flavoring; and
   a taste or cooling sensation communicated from said additive materials and imparted to said user providing means for encouraging increased use of said dental floss apparatus through the provision of positive reinforcement provided by said taste during use.

5. The dental floss apparatus of claim 2 wherein said handles configured for engagement with the fingers of a user comprise:
   each of said pair of handles being substantially planar;
   an aperture communicating between opposing first and second surfaces of each respective handle of said pair of handles; and
   said aperture dimensioned for an engagement with one or a plurality of fingers of a user therein.

6. The dental floss apparatus of claim 5, additionally comprising:
   said dissolvable substrate having one or a combination of additive materials from a group consisting of mouthwash, breath freshener, cooling agent and flavoring; and
   a taste or cooling sensation communicated from said additive materials and imparted to said user providing means for encouraging increased use of said dental floss apparatus through the provision of positive reinforcement provided by said taste during use.

7. The dental floss apparatus of claim 2, additionally comprising:
   said dental floss apparatus positioned within a cavity defined by sidewalls of a package;
   said package openable by a tearing of a sidewall; and
   said package providing means for maintaining said dental floss apparatus substantially sterile during travel or transport and until employed.

8. The dental floss apparatus of claim 7, additionally comprising:
   said dissolvable substrate having one or a combination of additive materials from a group consisting of mouthwash, breath freshener, cooling agent and flavoring; and
   a taste or cooling sensation communicated from said additive materials and imparted to said user providing means for encouraging increased use of said dental floss apparatus through the provision of positive reinforcement provided by said taste during use.

9. The dental floss apparatus of claim 2, additionally comprising:
   said dissolvable substrate having one or a combination of additive materials from a group consisting of mouthwash, breath freshener, cooling agent and flavoring; and
   a taste or cooling sensation communicated from said additive materials and imparted to said user providing means for encouraging increased use of said dental floss apparatus through the provision of positive reinforcement provided by said taste during use.

10. The dental floss apparatus of claim 1, additionally comprising:
    said dissolvable substrate being formed of material having a fluorescence when contacted by light; and
    an enhanced contrast between said distal ends of said dissolvable substrate having said fluorescence, and said central gap therebetween, providing a visually enhanced said means for targeting said flossing substrate.

11. The dental floss apparatus of claim 10 wherein said handles configured for engagement with the fingers of a user comprise:
    each of said pair of handles being substantially planar; and
    opposing surfaces on each of said pair of handles sized for a contact with one of a finger and a thumb of a user thereon in a frictional engagement thereto.

12. The dental floss apparatus of claim 11, additionally comprising:
    said dental floss apparatus positioned within a cavity defined by sidewalls of a package;
    said package openable by a tearing of a sidewall; and
    said package providing means for maintaining said dental floss apparatus substantially sterile during travel or transport and until employed.

13. The dental floss apparatus of claim 10 wherein said handles configured for engagement with the fingers of a user comprise:
    each of said pair of handles being substantially planar;
    an aperture communicating between opposing first and second surfaces of each respective handle of said pair of handles; and
    said aperture dimensioned for an engagement with one or a plurality of fingers of a user therein.

14. The dental floss apparatus of claim 10, additionally comprising:
    said dental floss apparatus positioned within a cavity defined by sidewalls of a package;
    said package openable by a tearing of a sidewall; and
    said package providing means for maintaining said dental floss apparatus substantially sterile during travel or transport and until employed.

15. The dental floss apparatus of claim 1 wherein said handles configured for engagement with the fingers of a user comprise:
    each of said pair of handles being substantially planar; and
    opposing surfaces on each of said pair of handles sized for a contact with one of a finger and a thumb of a user thereon in a frictional engagement thereto.

16. The dental floss apparatus of claim 1 wherein said handles configured for engagement with the fingers of a user comprise:
    each of said pair of handles being substantially planar;
    an aperture communicating between opposing first and second surfaces of each respective handle of said pair of handles; and
    said aperture dimensioned for an engagement with one or a plurality of fingers of a user therein.

17. The dental floss apparatus of claim 1, additionally comprising:
    said dental floss apparatus positioned within a cavity defined by sidewalls of a package;
    said package openable by a tearing of a sidewall; and
    said package providing means for maintaining said dental floss apparatus substantially sterile during travel or transport and until employed.

* * * * *

UNITED STATES PATENT AND TRADEMARK OFFICE
CERTIFICATE OF CORRECTION

| | |
|---|---|
| PATENT NO. | : 8,381,742 B2 |
| APPLICATION NO. | : 13/012105 |
| DATED | : February 26, 2013 |
| INVENTOR(S) | : Leonard G. Lorch |

It is certified that error appears in the above-identified patent and that said Letters Patent is hereby corrected as shown below:

On the Title Page, Inventor, Item (76):

Error:
Inventor:    Leonard G. Lorch, ~~Mill Valley~~, CA

Correction:
Inventor:    Leonard G. Lorch, <u>San Rafael</u>, CA

Signed and Sealed this
Seventh Day of May, 2013

Teresa Stanek Rea
*Acting Director of the United States Patent and Trademark Office*